(12) United States Patent
Kimura et al.

(10) Patent No.: US 6,172,181 B1
(45) Date of Patent: Jan. 9, 2001

(54) (2,3,4,5,6-PENTAFLUOROBENZOYL) DIPHENYL ETHER COMPOUND, AND FLUORINE-CONTAINING ARYL ETHER KETONE POLYMER

(75) Inventors: Kunio Kimura, Okayama; Yuhiko Yamashita, Okayama-ken, both of (JP); Patrick E. Cassidy, Austin, TX (US); John W. Fitch, III; V. Sreenivasulu Reddy, both of San Marcos, TX (US)

(73) Assignee: Nippon Shokubai Co., Ltd., Osaka (JP)

( * ) Notice: Under 35 U.S.C. 154(b), the term of this patent shall be extended for 0 days.

(21) Appl. No.: 09/354,976

(22) Filed: Jul. 16, 1999

Related U.S. Application Data

(63) Continuation-in-part of application No. 09/106,270, filed on Jun. 29, 1998, now abandoned.

(51) Int. Cl.[7] .................................................... C08G 73/24

(52) U.S. Cl. .......................... 528/401; 528/397; 528/205; 528/206; 528/220

(58) Field of Search .................................... 528/401, 397, 528/205, 206, 220

(56) References Cited

PUBLICATIONS

Cassidy et al., "Polymers Derived from Hexafluoroacetone", JMS–Rev. Macromol. Chem. Phys., c29(2&3), 365–429 (1989).

Kimura et al., "New Polymers Derived from 2,3,4,5,6-pentafluorobenzoic Acid", Chemical Abstract 129:260978, 1999.

Mercer et al., "Synthesis and Characterization of Fluorinated Polyetherketones Prepared From Decafluorobenzophenone", Polymer, vol. 38, No. 8, pp. 1989–1995, (1997).

Tullos, et al., "Polymers Derived from Hexafluoroacetone: 12F–Poly(ether ketone)", Macromolecules, vol. 24, pp. 6059–6064 (1991).

*Primary Examiner*—Duc Truong
(74) *Attorney, Agent, or Firm*—Fish & Richardson P.C.

(57) ABSTRACT

A (2,3,4,5,6-pentafluorobenzoyl)diphenyl ether compound represented by the formula (I):

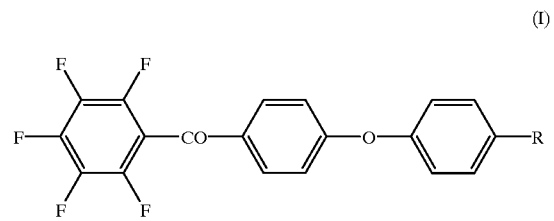

wherein R stands for a hydroxyl group or a group represented by

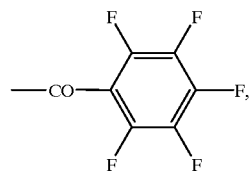

ether ketone polymer represented by the formula (II):

wherein n stands for a degree of polymerization, m is an integer of 0 or 1, and $R^1$ stands for a group represented by the formula (III):
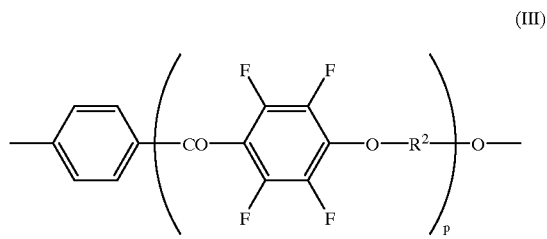
(III)
wherein p is an integer 0 or 1 and $R^2$ stands for
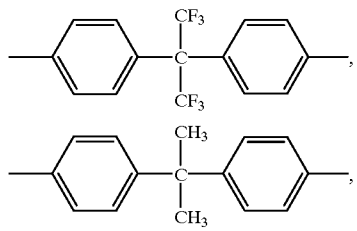
-continued
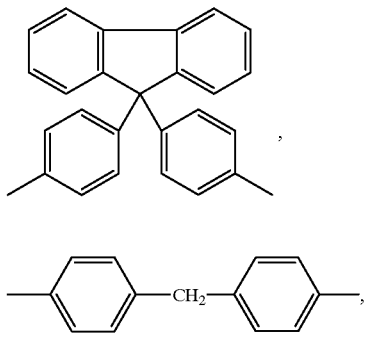
7 Claims, 10 Drawing Sheets

(2,3,4,5,6-PENTAFLUOROBENZOYL) DIPHENYL ETHER COMPOUND, AND FLUORINE-CONTAINING ARYL ETHER KETONE POLYMER

RELATED APPLICATION

This application is a continuation-in-part of application Ser. No. 09/106,270, filed Jun. 29, 1998, now abandoned.

BACKGROUND OF THE INVENTION

1. Field of the Invention

This invention relates to a novel (2,3,4,5,6-pentafluorobenzoyl) diphenyl ether compound and a novel fluorine-containing aryl ether ketone polymer.

2. Description of the Related Art

The high-performance fluorinated polymers have been receiving considerable attention as interesting advanced materials for applications as films, coatings for optical and microelectronics devices, gas separation membranes and so on (Cassidy, P. E., Aminabbai, T. M. and Farley, J. M., *J. Macromol. Sci.-Rev. Macromol. Chem. Phys.* C29 (2 & 3), 365–429 (1989)). The incorporation of fluorine atoms into polymer chains leads to polymers with increased solubility, flame resistance, thermal stability and glass transition temperature while also leading to decreased color, crystallinity, dielectric constant and moisture absorption. Owing these advantages, poly(aryl ether ketone)s (PEK) containing hexafluoroisopropylidene units had been prepared and studied for the use in aerospace and electronic applications (Tullos, G. L. and Cassidy, P. E., *Macromolecules*, 24, 6059 (1991)). Recently, PEK's containing perfluophenylene moieties were synthesized from perfluorobenzophenone (Mercer, F. W., Fone, M. M., Reddy, V. N., and Goodwin, A. A., *Polymer*, 38 (8), 1989 (1997)).

These polymers, however, are still deficient in solubility and flame resistance.

An object of this invention, therefore, is to provide a novel (2,3,4,5,6-pentafluorobenzoyl)diphenyl ether compound for the use as a raw material of a novel fluorine-containing aryl ether ketone polymer exhibiting high mechanical strength and toughness and excelling in electrical properties, thermal oxidative stability, and solubility.

Another object of this invention is to provide a novel fluorine-containing aryl ether ketone polymer.

Yet another object of this invention is to provide a fluorine-containing aryl ether ketone polymer exhibiting high mechanical strength and toughness and excelling in electrical properties, thermal oxidative stability, and solubility.

SUMMARY OF THE INVENTION

These objects can be accomplished by the following items (1) and (2).

(1) A (2,3,4,5,6-pentafluorobenzoyl)diphenyl ether compound represented by the formula (I):

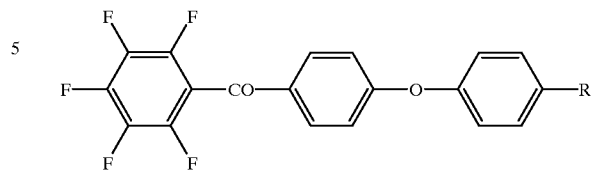

wherein R stands for a hydroxyl group or a group represented by the formula:

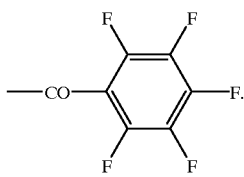

(2) A fluorine-containing aryl ether ketone polymer represented by the formula (II):

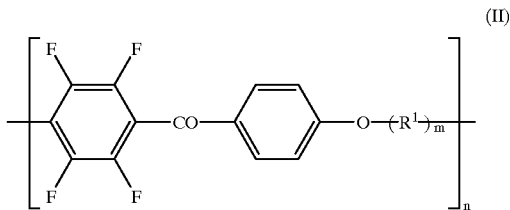

wherein n stands for a degree of polymerization, m is an integer of 0 or 1, and $R^1$ stands for a group represented by the formula (III):

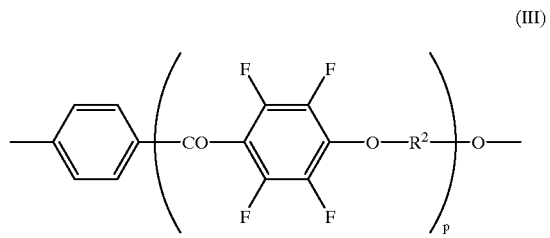

wherein p is an integer 0 or 1 and $R^2$ stands for

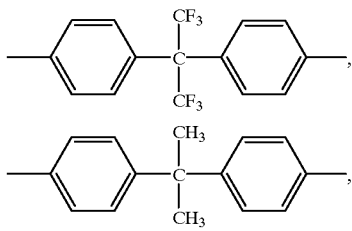

-continued

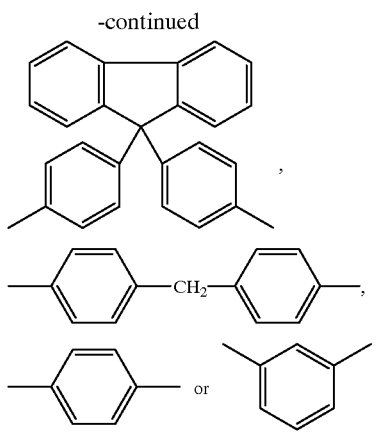

The (2,3,4,5,6-pentafluorobenzoyl)diphenyl ether compound of this invention, by being subjected to the reaction of polycondensation or to the reaction of co-condensation polymerization with a divalent phenol compound as described specifically herein below, can provide a novel fluorine-containing aryl ether ketone polymer exhibiting high mechanical strength and toughness and excelling in electrical properties, thermal oxidative stability, and solubility.

The fluorine-containing aryl ether ketone polymer of this invention are not only useful as a coating agent for electronic parts but also suitable for cast products because they possess high mechanical strength and toughness, excellent electrical properties, perfect solubility in various solvents in popular use, excellent thermal stability such as heat resistance and flame resistance, and excellent film-forming ability.

The above and other objects, features and advantages of the present invention will become clear from the following description of the preferred embodiments.

DESCRIPTION OF THE PREFERRED EMBODIMENTS

Figure 1:
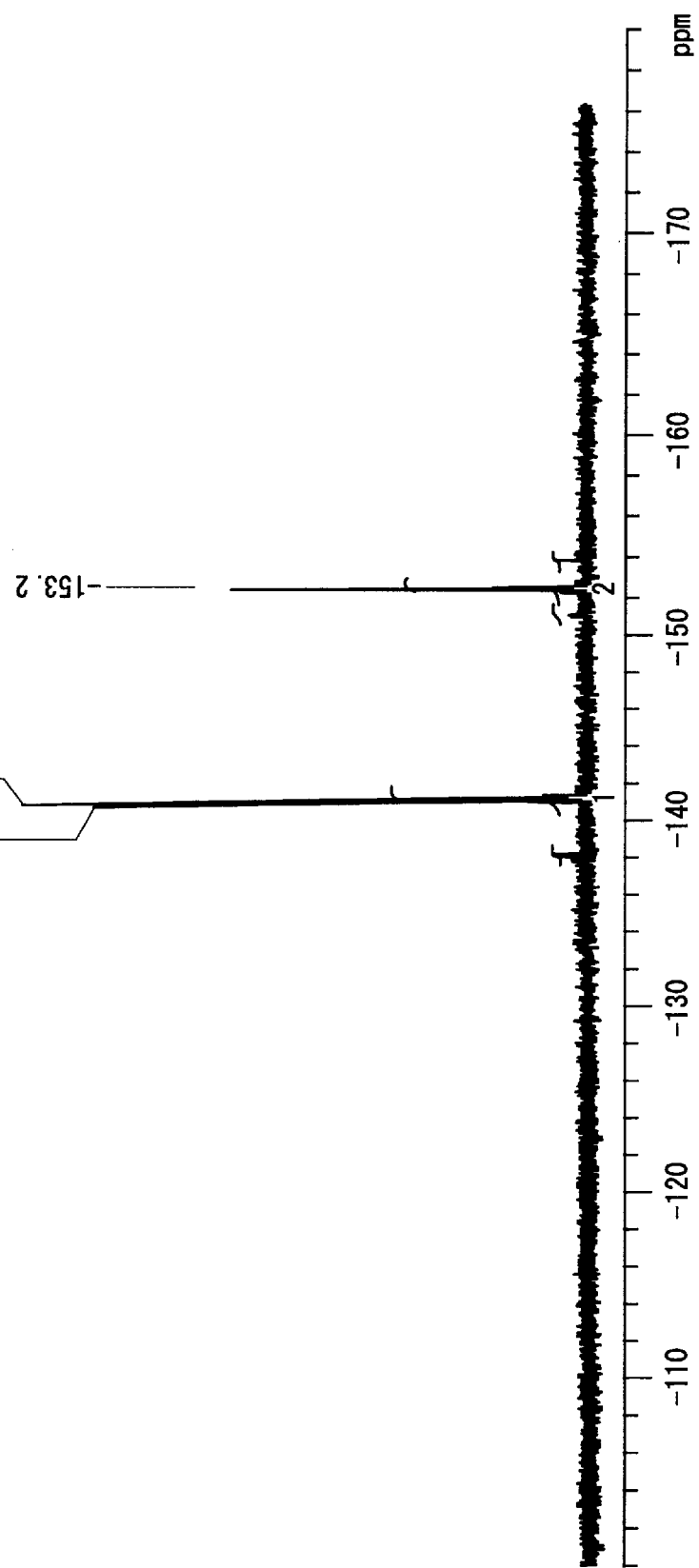
FIG. 1 is a $^{19}$F-NMR spectrum of 4F-PEEK to be obtained in Example 11.

The (2,3,4,5, 6-pentafluorobenzoyl)diphenyl ether compound of this invention is a novel compound represented by the formula (I):

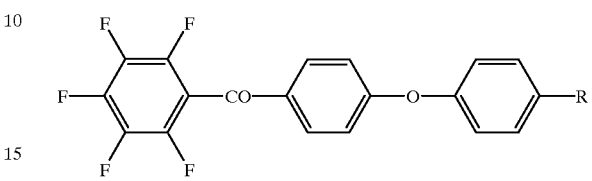

(I)

wherein R stands for a hydroxyl group (—OH) or a group represented by the formula :

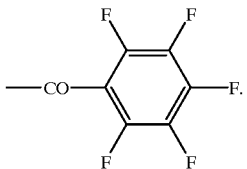

The formula (I), when R stands for a hydroxyl group (—OH), denotes 4-hydroxy-4'-(2,3,4,5,6-pentafluorobenzoyl)diphenyl ether (hereinafter referred to briefly as "HPDE") which is represented by the following formula (VII):

(VII)

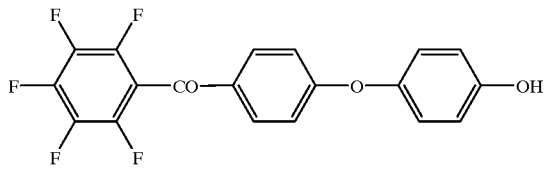

On the other hand, the formula (I), when R stands for a group of the formula:

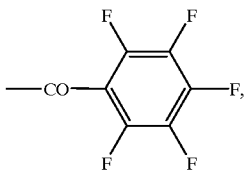

denotes 4,4'-bis(2,3,4,5,6-pentafluorobenzoyl)diphenyl ether (hereinafter referred to briefly as "BPDE") which is represented by the following formula (VIII):

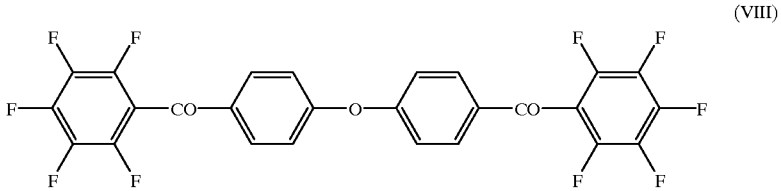
(VIII)

The HPDE represented by the formula (VII) is obtained by subjecting 2,3,4,5,6-pentafluorobenzoyl chloride to Friedel-Crafts reaction with 4-alkoxydiphenylether in an organic solvent and further subjecting the reaction product to dealkylation reaction. As concrete examples of the 4-alkoxydiphenylether, 4-methoxydiphenylether and 4-ethoxydiphenylether may be cited.

In the above Friedel-Crafts reaction, the amount of the 4-alkoxydiphenylether to be used per mol of 2,3,4,5,6-pentafluorobenzoyl chloride is in the range of 0.8 to 1.2 mols, preferably 0.9 to 1.1 mols. If this amount is less than 0.8 mol, then a 2,3,4,5,6-pentafluorobenzoyl group would be introduced excessively into the 4-alkoxydiphenylether. On the other hand, if it exceeds 1.2 mols, then the 4-alkoxydiphenylether suffered to remain in the unaltered form would be in such an unduly large amount as is unfavorable from the point of view of productivity.

As concrete examples of the Friedel-Crafts catalyst which may be effectively usable herein, aluminum chloride, antimony chloride, ferric chloride, ferrous chloride, titanium tetrachloride, boron trifluoride, tin tetrachloride, bismuth chloride, zinc chloride, mercury chloride, and sulfuric acid may be cited. The amount of this catalyst to be used is in the range of 0.5 to 10 mols, preferably 1 to 5 mols, per mol of the 2,3,4,5,6-pentafluorobenzoyl chloride.

The organic solvent to be used herein is required to be incapable of reacting with an acid chloride. As concrete examples of the organic solvent, dichloromethane, dichloroethane, carbon tetrachloride, carbon disulfide, and nitrobenzene may be cited. The concentration of the 2,3,4,5,6-pentafluorobenzoyl chloride in the organic solvent may be in the range of 1 to 50% by weight, preferably 5 to 30% by weight. The reaction may be carried out at a temperature in the range of 0° to 150° C., preferably 0° to 100° C., with the reaction system kept in a stirred state.

The product by this reaction may be obtained by pouring water into the reaction mixture, extracting the reaction product with such an extracting agent as dichloromethane, dichloroethane, or carbon tetrachloride, then separating an organic layer from the extract, and expelling the extracting agent by distillation. Then, it may be optionally recrystallized from methanol or ethanol to obtain as white crystals.

Now, the dealkylating treatment will be described below. To be specific, it can be implemented with an acid, alkali, or organic metal reagent, for example. As concrete examples of the reagent, hydrogen bromide, hydrogen iodide, trifluoroacetic acid, hydrochloride of pyridine, concentrated hydrochloric acid, magnesium iodide etherate, aluminum chloride, aluminum bromide, boron trichloride, boron triiodide, potassium hydroxide, and Grignard reagent may be cited. The amount of the reagent to be used is not less than 0.1 mol, preferably in the range of 0.1 to 30 mols, per mol of the 4-alkoxy-4'-(2,3,4,5,6-pentafluorobenzoyl)diphenyl ether.

In this invention, the dealkylating reaction may be carried out either in the absence of a solvent or in a solvent. In consideration with the reaction efficiency and controllability of the reaction, the reaction may be preferably carried out in a solvent.

The solvents which may be effectively used in the case of carrying out the dealkylating reaction therein include water, acetic acid, acetic anhydride, benzene, and tetrahydrofuran, for example. The concentration of the 4-alkoxy-4'-(2,3,4,5,6-pentafluorobenzoyl) diphenyl ether in the solvent may be in the range of 1 to 50% by weight, preferably 5 to 30% by weight. The reaction may be performed at a temperature in the range of 0° to 250° C., preferably 50° to 200° C.

The BPDE represented by the formula (VIII) may be obtained by causing 2,3,4,5,6-pentafluorobenzoyl chloride to react with diphenyl ether in an organic solvent in the presence of a Friedel-Crafts catalyst. The amount of the diphenyl ether to be used per mol of the 2,3,4,5, 6-pentafluorobenzoyl chloride is in the range of 0.4 to 0.6 mol, preferably 0.45 to 0.55 mol. If this amount is less than 0.4 mol, then a 2,3,4,5,6-pentafluorobenzoyl group would be introduced into the diphenyl ether excessively. On the other hand, if it exceeds 0.6 mol, then the diphenyl ether suffered to remain in an unaltered form would be in such an unduly large amount as is unfavorable from the point of view of productivity.

As concrete examples of the Friedel-Crafts catalyst which may be effectively usable herein, aluminum chloride, antimony chloride, ferric chloride, ferrous chloride, titanium tetrachloride, boron trifluoride, tin tetrachloride, bismuth chloride, zinc chloride, mercury chloride, and sulfuric acid may be cited. The amount of this catalyst to be used is in the range of 0.5 to 10 mols, preferably 1 to 5 mols, per mol of the 2,3,4,5,6-pentafluorobenzoyl chloride.

As the organic solvent, a solvent which is incapable of reacting with an acid chloride can be used. As concrete examples of the solvent, dichloromethane, dichloroethane, carbon tetrachloride, carbon disulfide, and nitrobenzene may be cited. The concentration of the 2,3,4,5,6-pentafluorobenzoyl chloride in the organic solvent may be in the range of 1 to 50% by weight, preferably 5 to 30% by weight.

The reaction may be carried out at a temperature in the range of 0° to 150° C., preferably 0° to 100° C., with the reaction system kept in a stirred state. The product by this reaction may be obtained by pouring water into the reaction mixture, extracting the reaction product with such an extracting agent as dichloromethane, dichloroethane, or carbon tetrachloride, then separating an organic layer from the extract, and expelling the extracting agent by distillation. Then, it may be optionally recrystallized from methanol or ethanol to obtain as white crystals.

The fluorine-containing aryl ether ketone polymer according to this invention is a polymer represented by the formula (II):

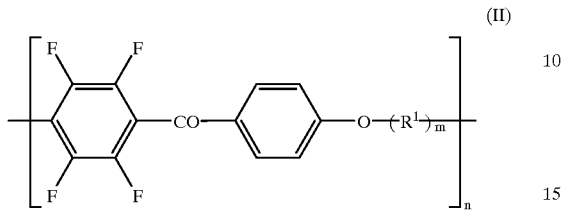

(II)

In this formula (II), $R^1$ and m are as defined above, and n stands for a degree of polymerization, and specifically in the range of 2 to 5000, preferably in the range of 5 to 500. Further, in this invention, the fluorine-containing aryl ether ketone polymer consists of the same repeating units or alternatively consists of the different repeating units. In the latter case, the repeating units may be either in a block form or a random form.

In this invention, it may be considered from the following description in which a method for producing the fluorine-containing aryl ether ketone polymer will be more specifically shown that the fluorine-containing aryl ether ketone polymer of the formula (II) contains a fluorine atom at one terminus on the side of the benzene ring containing fluorine atoms and a hydrogen atom at another terminus on the side of $R^1$. On other words, the fluorine-containing aryl ether ketone polymer of the formula (II) is considered to be represented by the formula (XI):

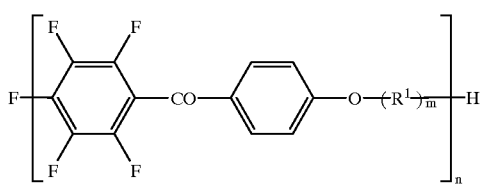

(XI)

This formula (II), when m is 0, denotes a fluorine-containing aryl ether ketone polymer represented by the formula (IV):

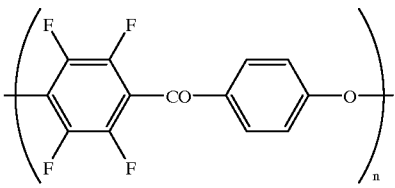

(IV)

wherein n stands for a degree of polymerization.

The formula (II), when m is 1 and p is 0, denotes a fluorine-containing aryl ether ketone polymer represented by the formula (V):

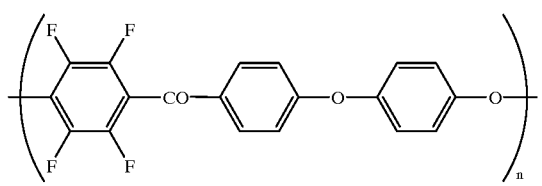

(V)

wherein n stands for a degree of polymerization.

The formula (II), when m is 1 and p is 1, denotes a fluorine-containing aryl ether ketone polymer represented by the formula (VI):

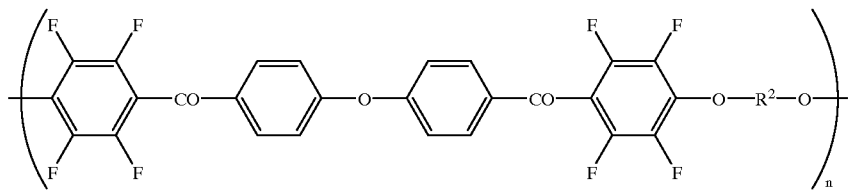

(VI)

wherein n represents a degree of polymerization and $R^2$ has the same meaning as mentioned above. In the above formula (VI), n is preferably in the range of 2 to 2000, more preferably in the range of 5 to 200.

The fluorine-containing aryl ether ketone polymers represented by the formulas (IV) and (V) may be obtained by heating a 2,3,4,5,6-pentafluorobenzoyl compound represented by the formula (IX):

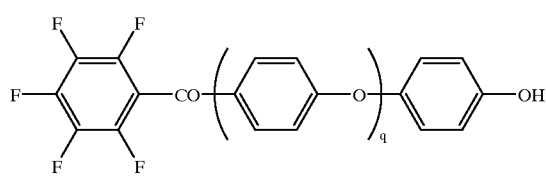 (IX)

wherein q is an integer of 0 or 1, in an organic solvent in the presence of a basic compound.

The temperature of this reaction may be in the range of 30° to 250° C., preferably 500 to 200° C.

The fluorine-containing aryl ether ketone polymer represented by the formula (VI):

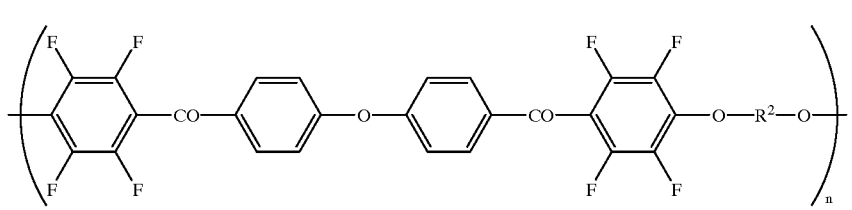 (VI)

wherein $R^2$ has the same meaning as mentioned above and n stands for a degree of polymerization, may be obtained by heating a 4,4'-bis(2,3,4,5,6-pentafluorobenzoyl)diphenyl ether represented by the formula (VIII):

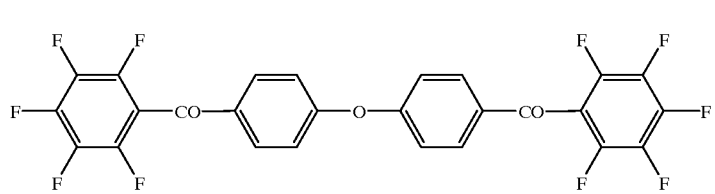 (VIII)

and a divalent phenol compound represented by the following formula (X):

HO—$R^2$—OH  (X)

wherein $R^2$ stands for

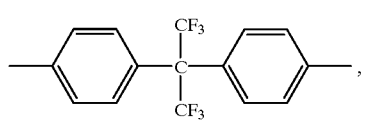

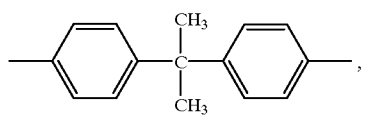

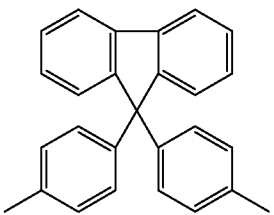

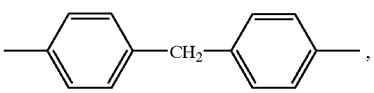

-continued

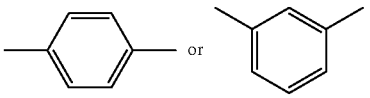 or in an organic solvent in the presence of a basic compound.

The reaction temperature may be in the range of 20° to 150° C., preferably 50° to 120° C. The low temperature used for the reaction may serve to repress otherwise possible secondary reactions and to prevent the polymer from gelation.

As concrete examples of the organic solvent to be used in any of the polymerization reactions contemplated by this invention, such polar solvents as N-methyl-2-pyrrolidinone and N,N-dimethyl acetamide, and methanol and toluene may be cited. These organic solvents may be used either singly or in the form of a mixture of two or more members.

The concentration of the pentafluorobenzoyl diphenyl ether compound in the organic solvent may be in the range of 5 to 50% by weight, preferably 10 to 30% by weight.

When toluene or other similar solvent is used in the initial stage of the reaction, the water which is by-produced during the formation of a phenoxide can be removed as an azeotrope of toluene without reference to the polymerization solvent.

The basic compound to be used in this invention functions to promote the reaction of polycondensation by collecting hydrogen fluorine formed by the reaction and, when the reaction of polycondensation occurs with a divalent phenol compound, also functions to convert the phenol compound into anions of higher reactivity.

As concrete examples of the basic compound, potassium carbonate, lithium carbonate, and potassium hydroxide may be cited.

The amount of the basic compound to be used, in the case of the polymers of the formulas (IV) and (V), is in the range of 0.5 to 10 mols, preferably 0.5 to 5 mols, per mol of the pentafluorobenzoyl diphenyl ether compound to be used, and in the case of the polymer of the formula (VI), in the range of 1 to 20 mols, preferably 1 to 10 mols, per mol of the pentafluorobenzoyl diphenyl ether compound to be used.

As concrete examples of the divalent phenol compound to be used in this invention, 2,2-bis(4-hydroxyphenyl)-1,1,1,3,3,3-hexafluoropropane (hereinafter referred to as "6FBA"), bisphenol A (hereinafter referred to as "BA"), 9,9-bis(4-hydroxyphenyl) fluorene (hereinafter referred to as "HF"), bisphenol F (hereinafter referred to as "BF"), hydroquinone (hereinafter referred to as "HQ"), and resorcinol (hereinafter referred to as "RS") may be cited. The amount of the divalent phenol compound to be used is in the range of 0.8 to 1.2 mols, preferably 0.9 to 1.1 mols, per mol of the 4,4'-bis(2,3,4,5,6-pentafluorobenzoyl) diphenyl ether.

After the reaction of polymerization has been completed, the polymer aimed at may be obtained by removing the solvent from the reaction solution as by distillation and, when necessary, refining the distillate. Alternatively, the polymer can be obtained by adding the reaction solution to a solvent in which the polymer exhibits a low solubility thereby causing the polymer to precipitate as a solid and separating the precipitate by filtration.

Now, this invention will be described more specifically below with reference to working examples.

In the working examples, physical properties were evaluated as following.

NMR spectra were recorded on an Varian Unity-500 operating at 500 MHz ($^1$H), 125 MHz ($^{13}$C) or 470 MHz ($^{19}$F). 4,4'-Difluorobenzophenone was used as an internal standard for $^{19}$F-NMR measurements.

Glass transition temperatures (Tg) and melting temperatures were measured on a Perkin-Elmer DSC 7 at a heating rate of 20° C./min Thermal stabilities were measured on a Perkin-Elmer TGA 7 at a heating rate of 20° C./min in a nitrogen atmosphere or in an air atmosphere.

Intrinsic viscosity measurements were carried out by using an Ostwald-Fenske viscometer in dimethylacetamide (DMAc) at a concentration of 0.5 dL/g and at 25° C.

Example 1

Synthesis of 2,3,4,5,6-pentafluoro-4'-hydroxybenzophenone

A round bottom flask provided with a condenser was supplied with 6.0 g of 2,3,4,5,6-pentafluoro-4'-methoxybenzophenone, 40 ml of glacial acetic acid, and 30 ml of an aqueous 48% hydrogen bromide solution. The resultant mixture was refluxed overnight and then cooled to a room temperature. The product was extracted from diethyl ether, dried with magnesium sulfate, filtered, and separated by distillation. It was recrystallized from toluene, to afford as white crystals 3.7 g (yield 78.8%) of 2,3,4,5,6-pentafluoro-4'-hydroxybenzophenone (hereinafter referred to as "HPBP"). The melting point of the product was 142° to 143° C. The NMR chemical shift of the crystals is shown in Table 1.

Example 2

Synthesis of 4-hydroxy-4'-(2,3,4,5,6-pentafluorobenzoyl) diphenyl ether

Into a 250 ml three-neck flask, which was equipped with an additional funnel and calcium chloride drying tube, were placed 4-ethoxydiphenyl ether (3.5 g), which was synthesized from p-phenoxyphenol with ethyl iodide in the presence of sodium hydroxide, aluminum chloride (5.4 g) and dried dichloroethane (30 ml). The solution of 2,3,4,5,6-pentafluorobenzoyl chloride (3.7 g), which was synthesized from 2,3,4,5,6-pentafluorobenzoic acid with thionyl chloride, and dried dichloroethane (10 ml) was slowly dripped into flask while stirring. After the addition was complete, the reaction mixture was stirred overnight at room temperature. Small amount of water was added very slowly to the reaction mixture and continued stirring for 15 min. The reaction mixture was then poured into 250 ml of water, which was extracted with dichloromethane. The organic layer was collected, washed with water, dried over sodium sulfate, filtered and evaporated. Recrystallization from methanol with charcoal yielded white crystal of 4-ethyoxy-4'-(2,3,4,5,6-pentafluorobenzoyl) diphenyl ehter (EPDE) (yield 60.4%).

EPDE (2.1 g), glacial acetic acid (14 ml) and 48% HBr (11 ml) were placed in flask, which was equipped with condenser. The mixture was refluxed overnight and allowed to cool to room temperature. The product was extracted with ether, dried over sodium sulfate, filtered and evaporated. Recrystallization from toluene yielded white crystal of 4-hydroxy-4'-(2,3,4,5,6-pentafluorobenzoyl)diphenyl ether (HPDE) (yield 78.8%). The melting point of HPDE is 136° to 137° C. The NMR chemical shift of the crystals is shown in Table 1.

TABLE 1

| | NMR chemical shifts[a)] of HPDE and BPDE | | | | | |
|---|---|---|---|---|---|---|
| | $^{19}$F chemical shift[b)] | | | $^{13}$C chemical shift[b)] | | |
| Compound | Ortho | Meta | Para | Ortho | Meta | Para |
| HPDE | −144.5 | −164.3 | −155.0 | 143.6 | 137.6 | 142.3 |
| BPDE | −144.3 | −164.0 | −154.5 | 143.7 | 137.6 | 142.5 |

[a)]$^{19}$F chemical shifts are reported in ppm relative to 4,4'-difluorobenzophenone = −110.1 ppm. $^{13}$C chemical shifts are reported in ppm relative to DMSO-d6 = 39.5 ppm.
[b)]Performed on dilute solutions in DMSO-d6.

Example 3

Synthesis of 4,4'-bis(2,3,4,5,6-pentafluorobenzoyl) diphenyl ether

Diphenyl ether (6.8 g), aluminum chloride (26.8 g) and dried dichloroethane (60 ml) were placed in 250 ml three-neck flask, which was equipped with an additional funnel and CaCl$_2$ drying tube. The solution of 2,3,4,5,6-pentafluorobenzoyl chloride (18.5 g) and dried dichloroethane (15 ml) was slowly dripped into flask while stirring. After the addition was complete, the reaction mixture was stirred overnight at room temperature. Small amount of water was added very slowly to the reaction mixture and continued stirring for 15 min. The reaction mixture was then poured into 250 ml of water, which was extracted with dichloromethane. The organic layer was collected, washed with water, dried over sodium sulfate, filtered and evaporated. Recrystallization from methanol with charcoal yielded white crystal of 4,4'-bis(2,3,4,5,6-pentafluorobenzoyl) diphenyl ether (BPDE) (yield 61.2%). The melting point of BPDE is 125° to 127° C. The NMR chemical shift of the crystals is shown in Table 1.

Example 4

HPBP (0.5 g), ground potassium carbonate (0.36 g), dimethyl acetamide (DMAc) (2 ml) and toluene (1 ml) were placed into a 25 ml of round-bottom flask equipped with Dean-Stark trap, condenser, magnetic stirrer and nitrogen inlet tube. The mixture was heated at 160 ° C. and toluene was distilled over. The mixture was ref luxed for 3 hours. After cooling, the solution was poured into rapid stirred water containing 1% acetic acid. The precipitated polymer was collected by filtration, washed with water and then dried. The yield of the produced compound was 90%. The viscosity of the compound measured in dimethyl acetamide at a concentration of 0.5 g/dL at a temperature of 25° C. was 0.18 dL/g. The insoluble content of this compound in dimethyl acetamide was found to be 11.5%.

Example 5

Figure 3:
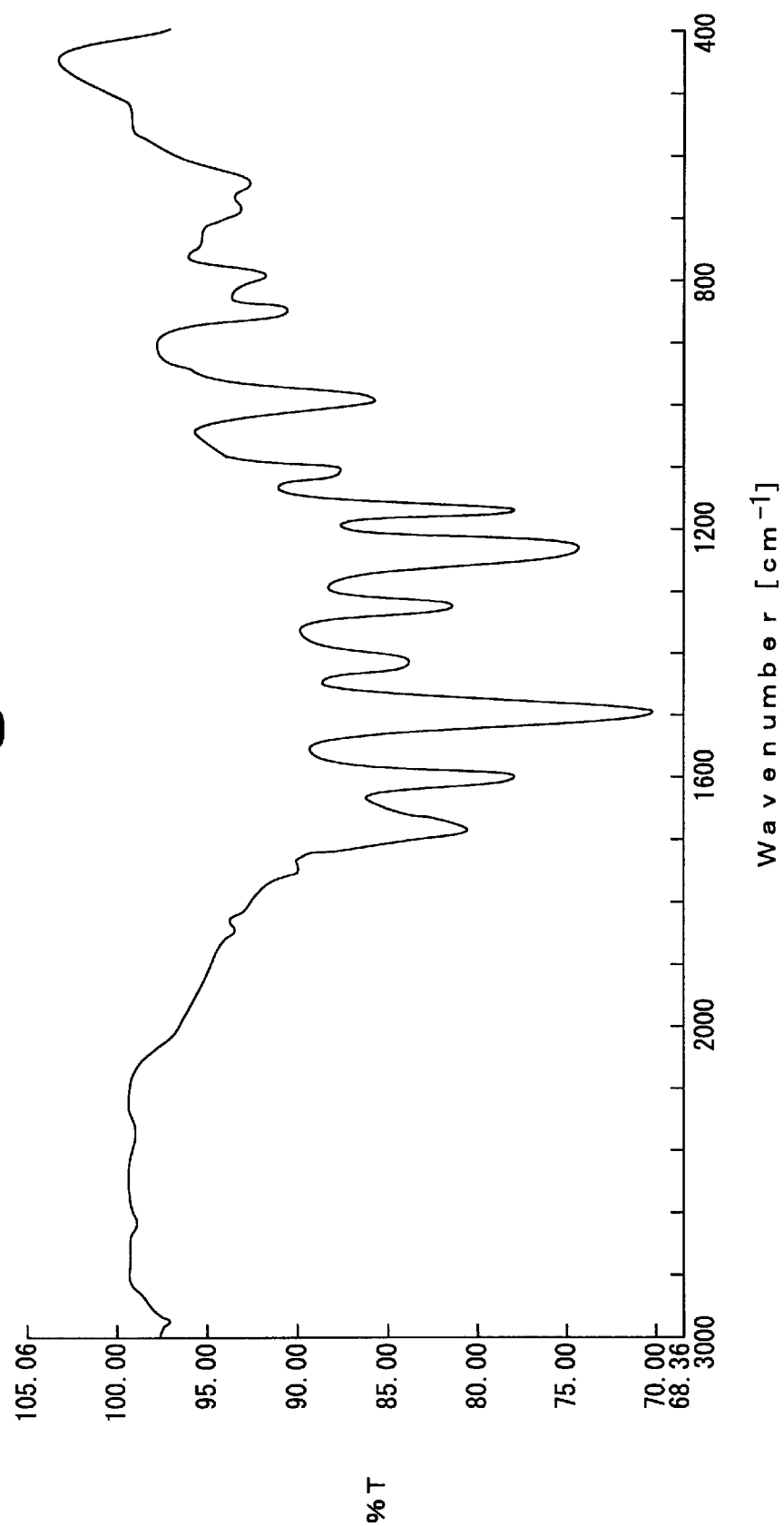
FIG. 3 is an IR spectrum of 4F-PEK to be obtained in Example 5.

A polymer of HPBP (hereinafter referred to as "4F-PEK") was produced by following the procedure of Example 4 while using N-methyl-2-pyrrolidinone instead of dimethyl acetamide. The yield was 85%, the viscosity 0.23 dL/g, and the insoluble content in dimethyl acetamide 6.0%. The IR spectrum of this 4F-PEK is shown in FIG. 3.

Examples 6 to 10

Polymers were produced by following the procedure of Example 4 while using 0.5 g of HPDE instead of 0.5 g of HPBP and performing the polymerization under the conditions shown in Table 2 instead. The results are shown in Table 2

TABLE 3

Solubility of 4F-PEK and 4F-PEEK

| Polymer | DMAc | NMP* | m-Cresol | Chloroform | Toluene | Methanol |
|---|---|---|---|---|---|---|
| 4F-PEK | ++ | ++ | ++ | – | – | – |
| 4F-PEEK | ++ | ++ | + | + | – | – |

++; soluble, +; partially soluble, ±; swollen, –; insoluble.

TABLE 4

Film-forming property of 4F-PEK and 4F-PEEK

| Item | 4F-PEK | 4F-PEEK |
|---|---|---|
| Film-forming property | ± | + |
| Rigidity | Extremely brittle | Weak |
| Hue | Dark brown | Brown |

1) Films were prepared by casting of 20 wt % DMAc solution.
2) ++; excellent, +; good, ±; poor, –; very poor.

TABLE 5

Thermal stability of 4F-PEK and 4F-PEEK

| Polymer | 10% loss in nitrogen (° C.) | Formation of carbide in nitrogen at 600° C. (wt %) | 10% loss in air (° C.) | Formation of carbide in air at 600° C. (wt %) |
|---|---|---|---|---|
| 4F-PEK | 443 | 58 | 421 | 52 |
| 4F-PEEK | 559 | 82 | 553 | 62 |

Note) TGA was performed with a heating rate of 20° C./min.

TABLE 2

Results of polymerization of HPDE

| Example | Basic compound | Concentration (%) | Temperature (° C.) | Duration (hours) | Viscosity* (dL/g) | Insoluble content in DMAc (%) | Yield (%) |
|---|---|---|---|---|---|---|---|
| 6 | K₂CO₃ | 25 | 120/80 | 2/20 | 0.23 | 0 | 81 |
| 7 | K₂CO₃ | 25 | 160 | 3 | 0.37 | 6.3 | 83 |
| 8 | K₂CO₃ | 25 | 120 | 20 | 0.18 | 0 | 80 |
| 9 | K₂CO₃ | 25 | 140 | 20 | 0.44 | 6.1 | 80 |
| 10 | K₂CO₃ | 10 | 160 | 3 | 0.21 | 0.6 | 80 |

*Viscosities were measured in DMAc at a concentration of 0.5 g/dL and at 25° C.

Example 11

Figure 4:
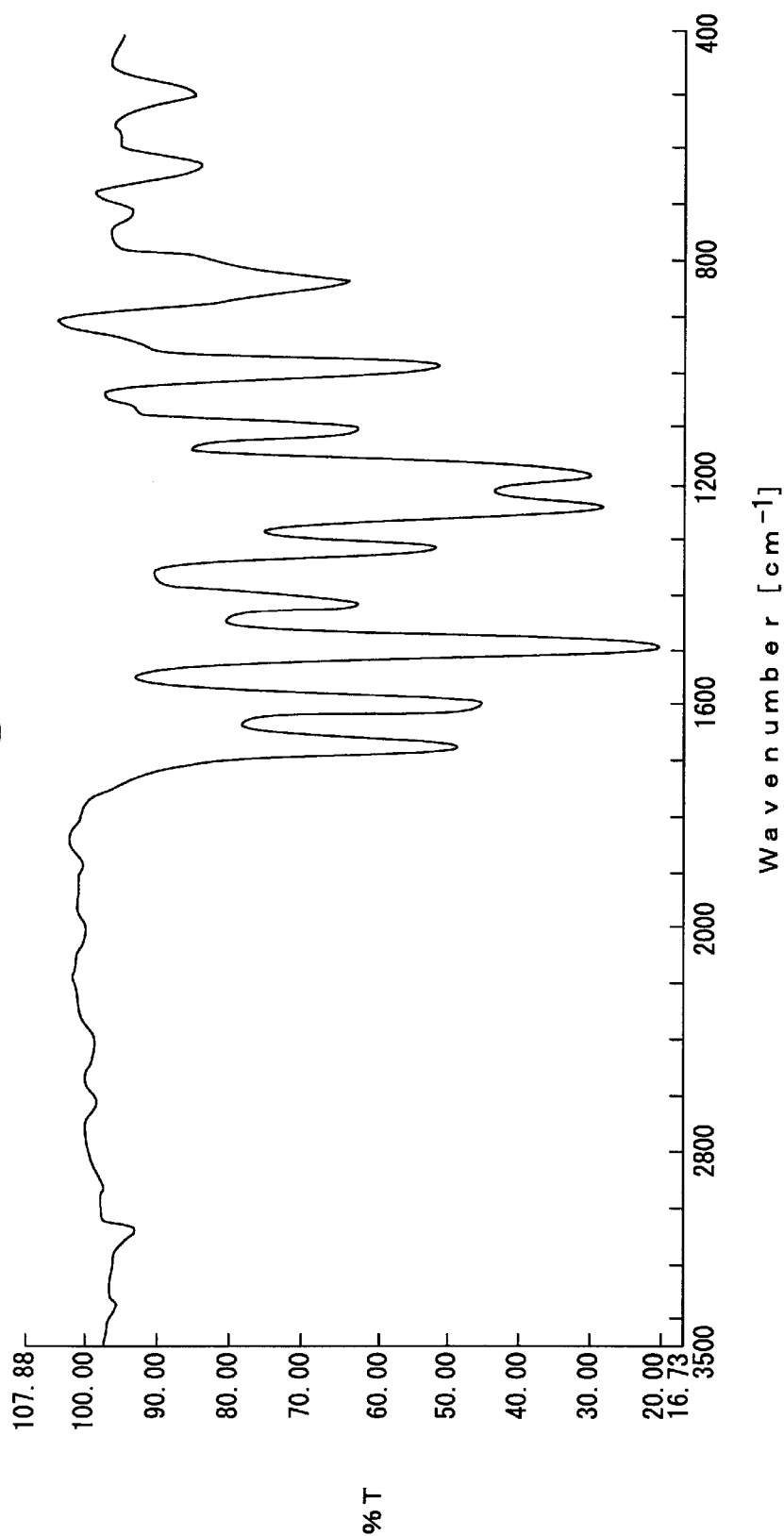
FIG. 4 is an IR spectrum of 4F-PEEK to be obtained in Example 11.
Figure 5:
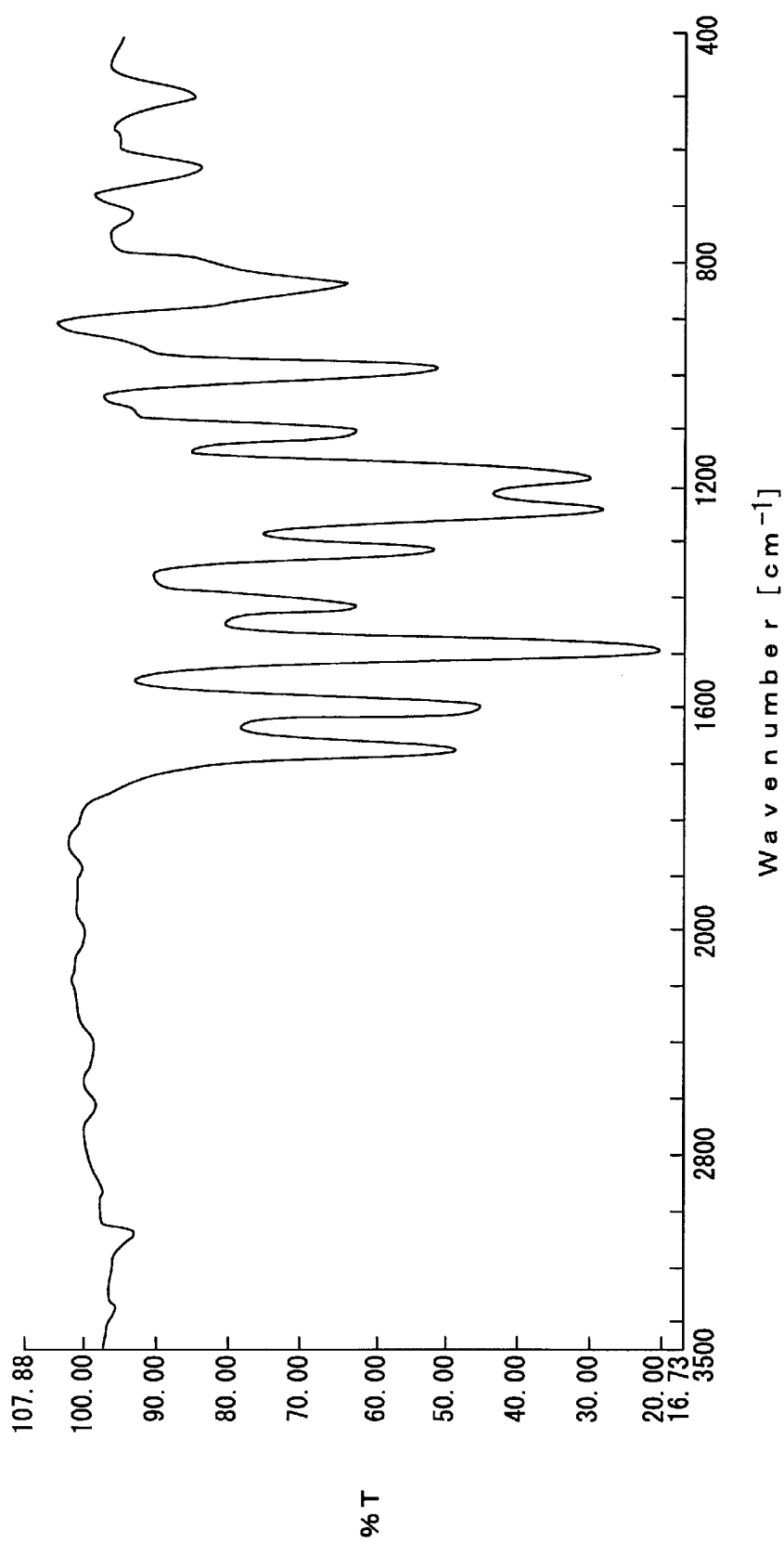
FIG. 5 is an IR spectrum of BPDE-6FBA to be obtained in Example 14.
Figure 6:
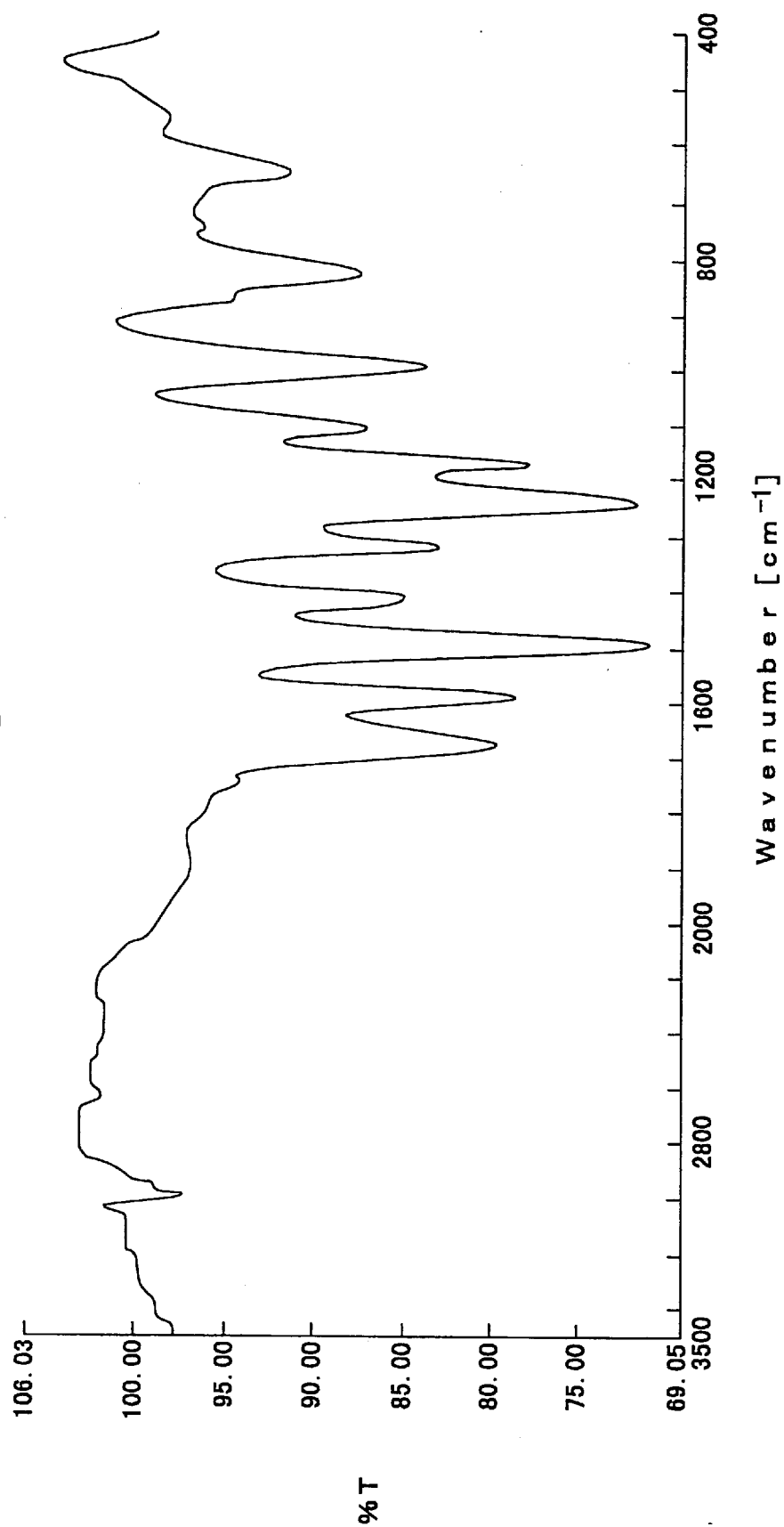
FIG. 6 is an IR spectrum of BPDE-BA to be obtained in Example 15.
Figure 7:
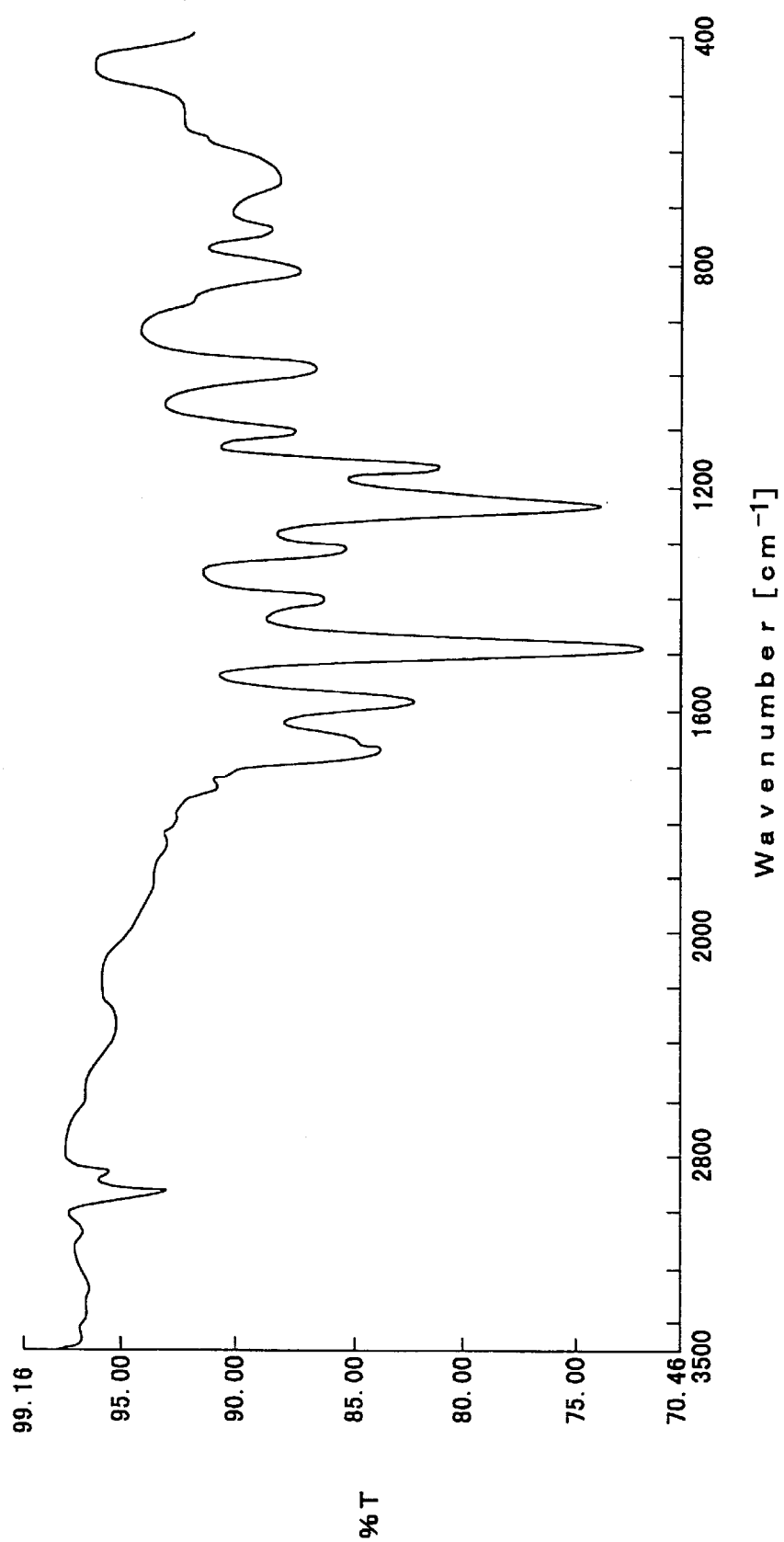
FIG. 7 is an IR spectrum of BPDE-HF to be obtained in Example 16.
Figure 8:
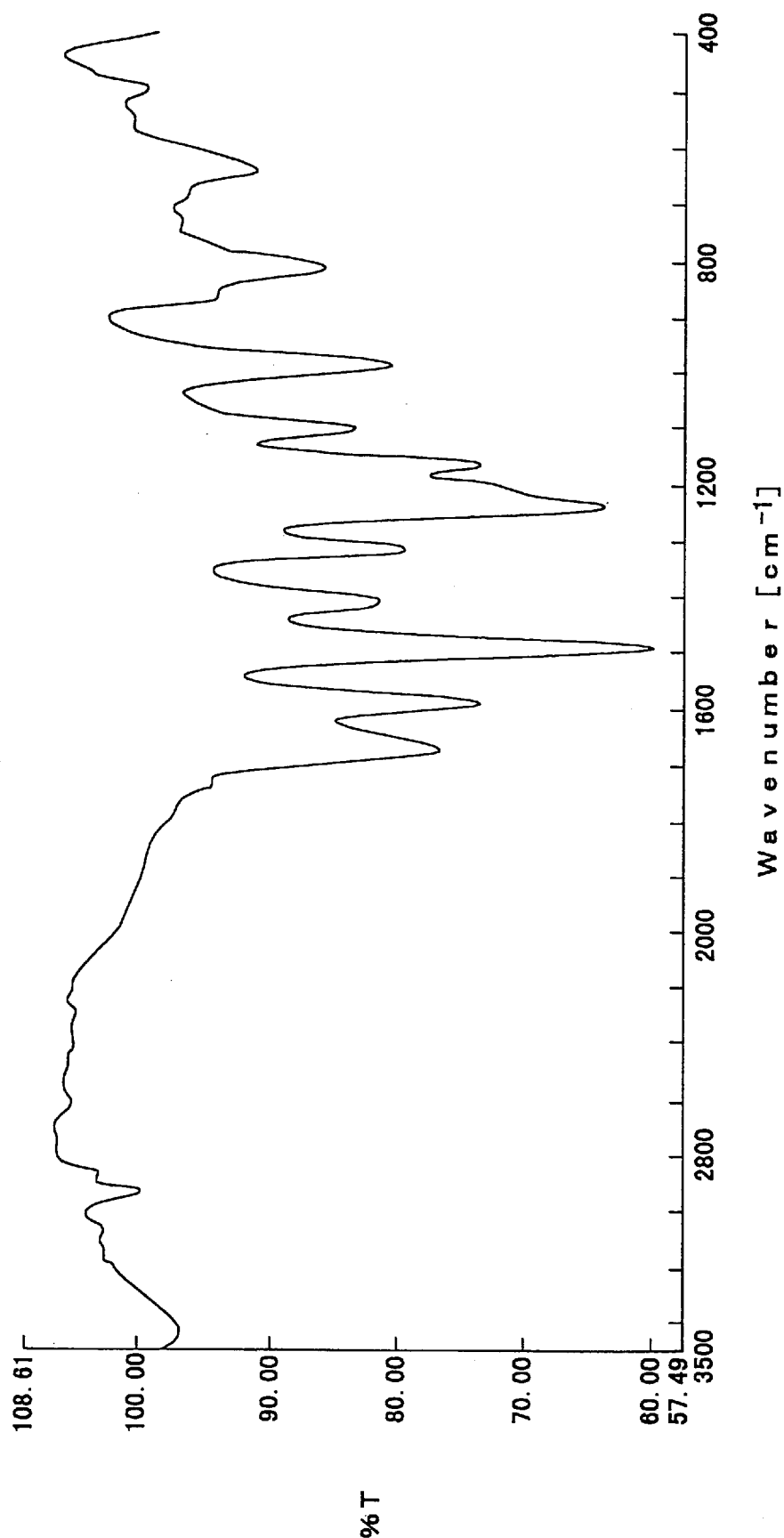
FIG. 8 is an IR spectrum of BPDE-BF to be obtained in Example 17.
Figure 9:
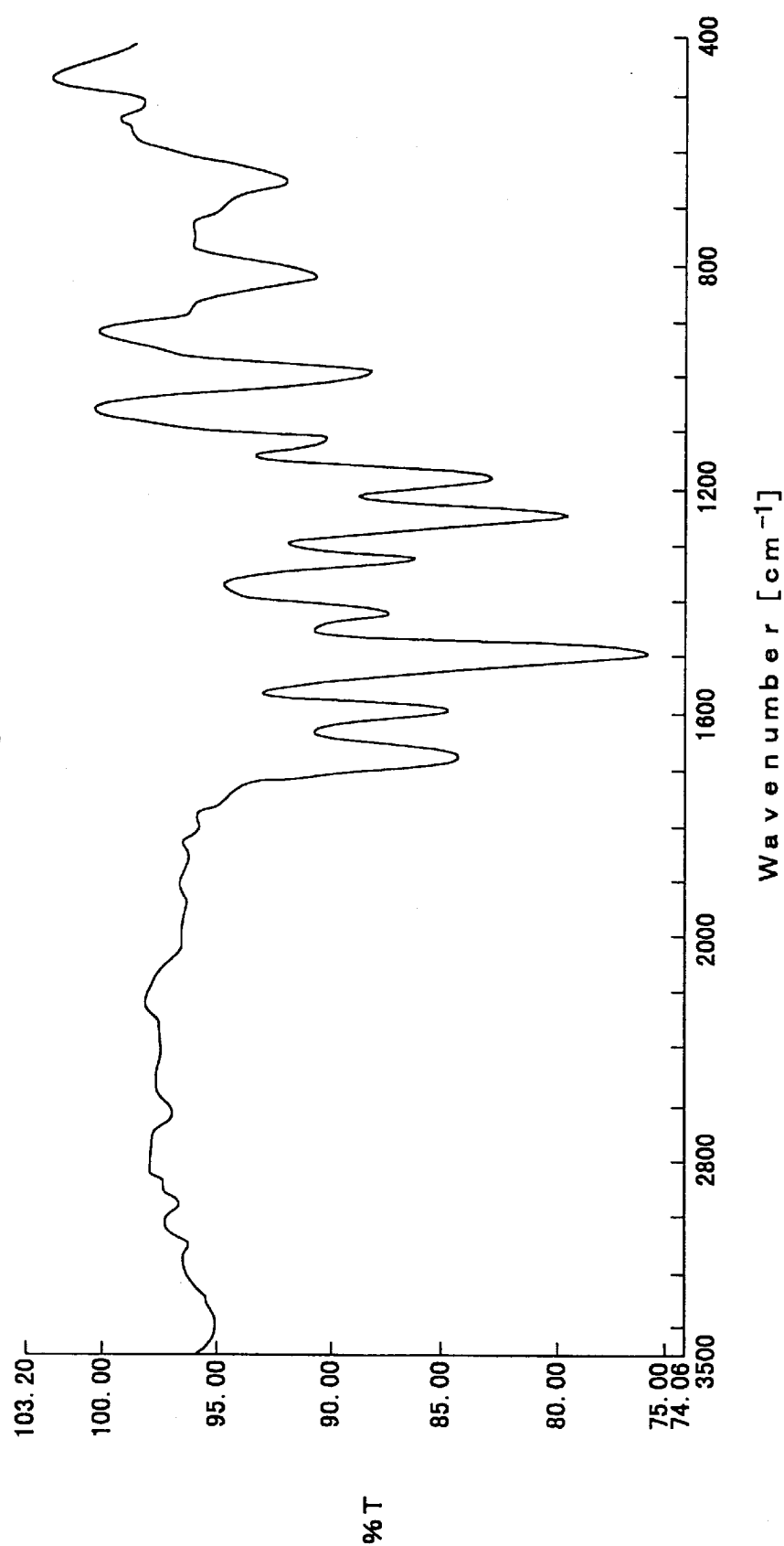
FIG. 9 is an IR spectrum of BPDE-HQ to be obtained in Example 18.
Figure 10:
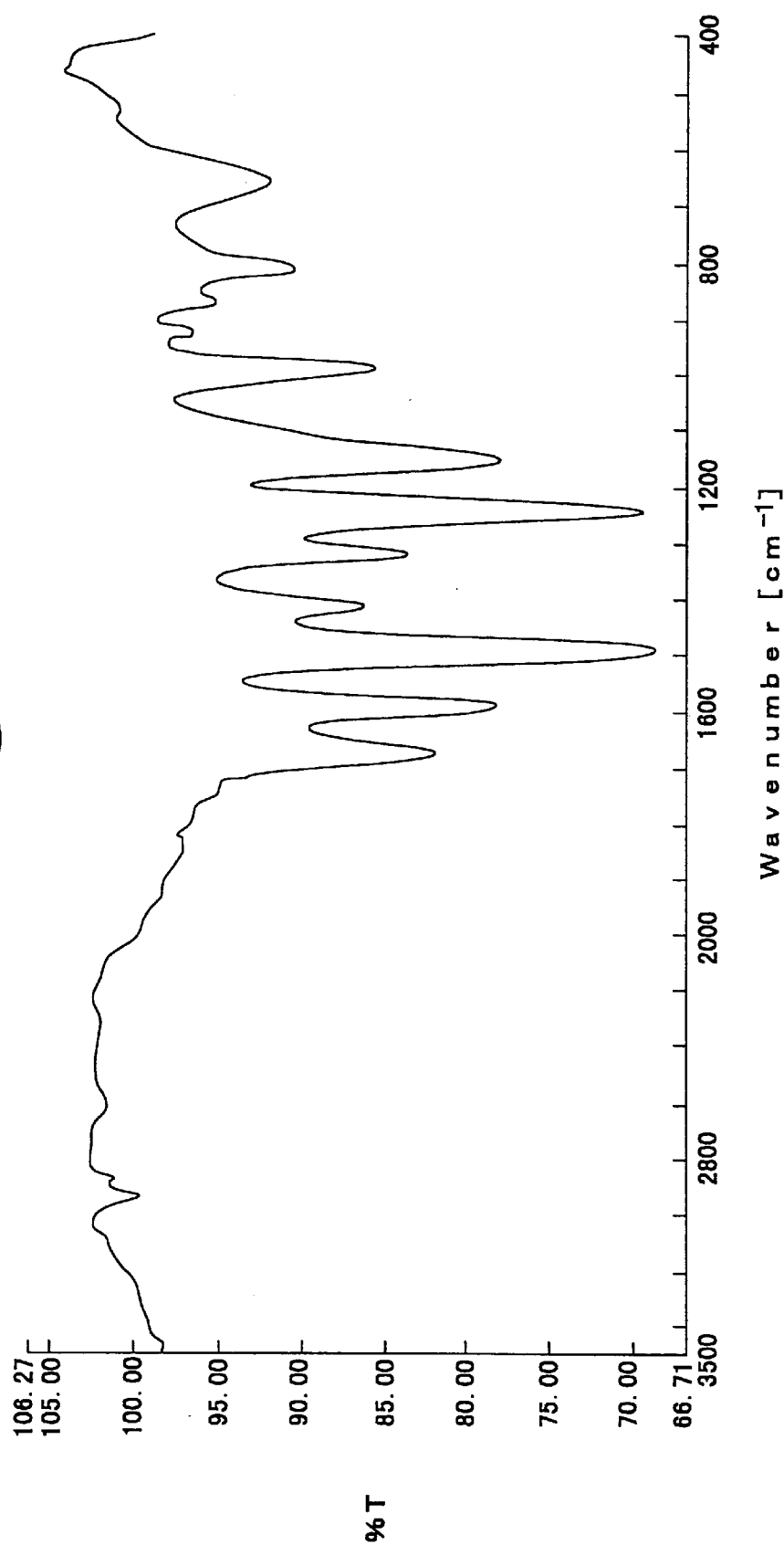
FIG. 10 is an a IR spectrum of BPDE-RS to be obtained in Example 19.

A polymer of HPDE (hereinafter referred to as "4F-PEEK") was produced by following the procedure of Example 4 while using 0.5 g of HPDE instead of 0.5 g of HPBP and using N-methyl-2-pyrrolidinone instead of dimethyl acetamide. The yield was 82%, the viscosity 0.53 dL/g, the insoluble content in dimethyl acetamide 0.2%. The $^{19}$F-NMR spectrum and IR spectrum of this 4F-PEEK are shown in FIG. 1 and FIG. 4, respectively. In the $^{19}$F-NMR spectrum, 19F chemical shifts are reported in ppm relative to 4,4'-difluorobenzophenone=–110.1 ppm.

Example 12

The 4F-PEK obtained in Example 5 and the 4F-PEEK obtained in Example 11 were tested for physical properties. The results are shown in Tables 3 to 6.

TABLE 6

DSC Data of 4F-PEK and 4F-PEEK

| Polymer | Tg (° C.) | Tm (° C.) |
|---|---|---|
| 4F-PEK | 181 | ND |
| 4F-PEEK | 166 | 285 |

1) DSC was performed with a heating rate of 20° C./min. from 50° to 350° C. under nitrogen.
2) ND; not detected.

Examples 13 to 19

Figure 2:
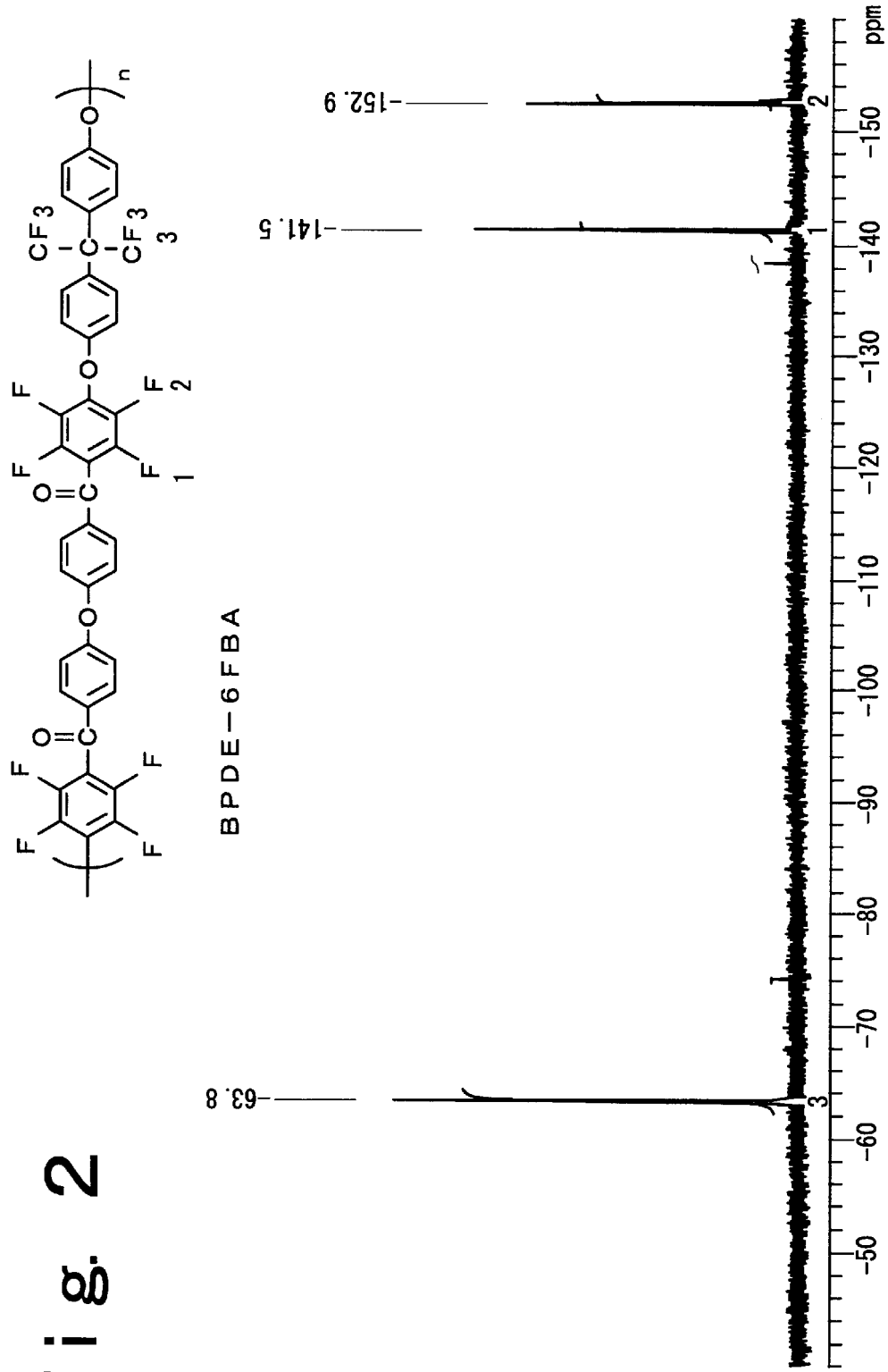
FIG. 2 is a $^{19}$F-NMR spectrum of BPDE-6FBA to be obtained in Example 14.

6FBA (1.2 g) (BA (0.82 g), HF (1.25 g), BF (0.71 g), HQ (0.39 g), or RS (0.39 g)) which was purified by recrystallization from toluene, ground potassium carbonate (1.48 g), DMAC (13 ml) and toluene (10 ml) were placed into a 100 ml of three-neck, round-bottom flask equipped with Dean-Stark trap, condenser, magnetic stirrer and nitrogen inlet tube. The mixture was heated at 160° C., allowed to reflux for 2 hours and then toluene was distilled over. BPDE (2.0 g) was added into the mixture and the polymerization was allowed to proceed under the conditions shown in Table 7. After cooling, the solution was poured into rapid stirred water containing 1% acetic acid. The precipitated polymer was collected by filtration, washed with water and then dried. The results are shown in Table 7. The $^{19}$F-NMR spectrum of the polymer to be obtained in Example 14 is shown in FIG. 2 and IR spectra of the polymers to be obtained in Examples 14 to 19 are shown in FIGS. 5 to 10, respectively. In the 19F-NMR spectrum, $^{19}$F chemical shifts are reported in ppm relative to 4,4'-difluorobenzophenone=−110.1 ppm.

TABLE 7

Results of polymerization

| Example | Polymer acronym | Concentration (%) | Temperature (° C.) | Duration (hours) | Viscosity* (dL/g) | Yield (%) |
|---|---|---|---|---|---|---|
| 13 | BPDE-6FBA | 25 | 80 | 20 | 0.22 | 91 |
| 14 | BPDE-6FBA | 25 | 100 | 20 | 0.31 | 92 |
| 15 | BPDE-BA | 25 | 80 | 20 | 0.19 | 90 |
| 16 | BPDE-HF | 25 | 80 | 20 | 0.37 | 99 |
| 17 | BPDE-BF | 25 | 80 | 20 | 0.35 | 93 |
| 18 | BPDE-HQ | 25 | 80 | 20 | 0.28 | 89 |
| 19 | BPDE-RS | 25 | 80 | 20 | 0.35 | 88 |

Note) Viscosities were measured in DMAc at a concentration of 0.5 g/dL and 25° C.
Asterisks show polymers containing insoluble parts.

Example 20

The polymers of BPDE to be obtained in Examples 14 to 19 (hereinafter referred to as "8F-PEKEK") were tested for physical properties. The results are shown in Tables 8 to 11.

TABLE 8

Solubility of 8F-PEKEK

| Example | Polymer acronym | DMAc | NMP* | m-Cresol | Chloroform | Toluene | Methanol |
|---|---|---|---|---|---|---|---|
| 14 | BPDE-6FBA | ++ | ++ | ++ | ++ | ++ | − |
| 15 | BPDE-BA | ++ | ++ | ++ | ++ | ++ | − |
| 16 | BPDE-HF | ++ | ++ | ++ | ++ | ++ | − |
| 17 | BPDE-BF | ++ | ++ | ± | + | − | − |
| 18 | BPDE-HQ | + | + | − | − | − | − |
| 19 | BPDE-RS | ++ | ++ | + | − | − | − |

Note) ++; soluble at room temperature, +; partially soluble, ±; swollen, −; insoluble.

TABLE 9

Film-forming property of 8F-PEKEK

| Example | Polymer acronym | Film-forming property | Rigidity | Hue |
|---|---|---|---|---|
| 14 | BPDE-6FBA | ++ | Tough | Brown |
| 15 | BPDE-BA | ++ | Tough | Light yellow |
| 16 | BPDE-HF | ++ | Tough | Light yellow |
| 17 | BPDE-BF | ++ | Tough | Light yellow |
| 18 | BPDE-HQ | + | Brittle | Brown |
| 19 | BPDE-RS | ++ | Tough | Brown |

1) Films were prepared by casting of 20 wt % DMAc solution.
2) ++; excellent, +; good, ±; poor, −; very poor.

TABLE 10

Thermal stability of 8F-PEKEK

| Example | Polymer acronym | 10% loss in nitrogen (° C.) | Formation of carbide in nitrogen at 600° C. (wt %) | 10% loss in air (° C.) | Formation of carbide in air at 600° C. (wt %) |
|---|---|---|---|---|---|
| 14 | BPDE-6FBA | 524 | 62 | 518 | 60 |
| 15 | BPDE-BA | 499 | 66 | 509 | 69 |
| 16 | BPDE-HF | 533 | 79 | 535 | 73 |
| 17 | BPDE-BF | 502 | 72 | 496 | 68 |
| 18 | BPDE-HQ | 524 | 70 | 505 | 59 |
| 19 | BPDE-RS | 599 | 90 | 544 | 66 |

Note) TGA was performed with a heating rate of 20° C./min.

TABLE 11

DSC data of 8F-PEKEK

| Example | Polymer acronym | Tg (° C.) | Tm (° C.) |
|---|---|---|---|
| 14 | BPDE-6FBA | 174 | ND |
| 15 | BPDE-BA | 170 | ND |
| 16 | BPDE-HF | 239 | ND |
| 17 | BPDE-BF | 162 | ND |
| 18 | BPDE-HQ | 163 | 327 |
| 19 | BPDE-RS | 152 | 338 |

1) DSC was performed with a heating rate of 20° C./min. from 50° to 350° C. under nitrogen.
2) ND; not detected.

What is claimed is:

1. A (2,3,4,5,6-pentafluorobenzoyl)diphenyl ether compound represented by the formula (I):

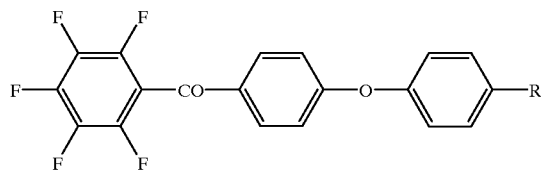
(I)

wherein R stands for a hydroxyl group or a group represented by the formula:

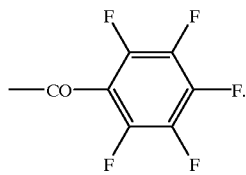

2. A (2,3,4,5,6-pentafluorobenzoyl)diphenyl ether compound according to claim 1, wherein R in the formula (I) stands for a hydroxyl group.

3. A (2,3,4,5,6-pentafluorobenzoyl)diphenyl ether compound according to claim 1, wherein R in the formula (I) stands for

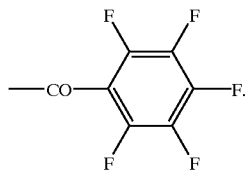

4. A fluorine-containing aryl ether ketone polymer represented by the formula (II):

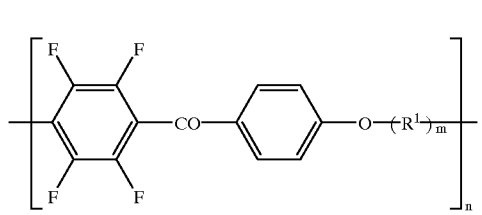
(II)

wherein n stands for a degree of polymerization, m is an integer of 0 or 1, and $R^1$ stands for a group represented by the formula (III):

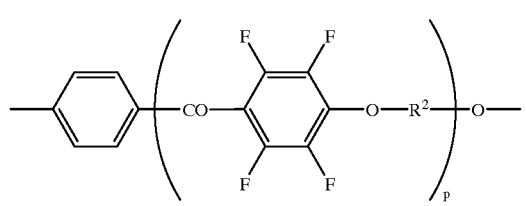
(III)

wherein p is an integer 0 or 1 and $R^2$ stands for

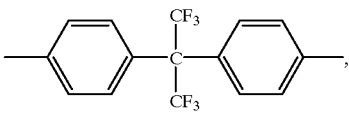

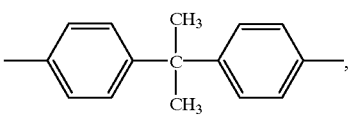

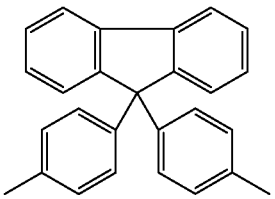

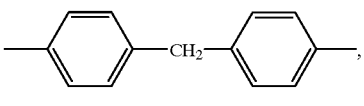

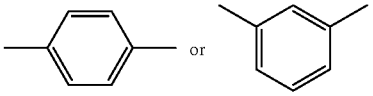

5. A fluorine-containing aryl ether ketone polymer according to claim 4 and represented by the formula (IV):

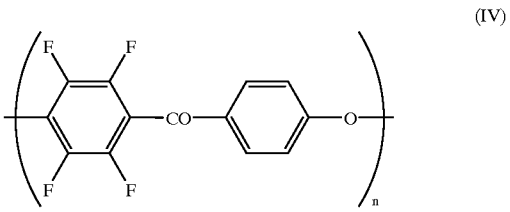
(IV)

wherein n stands for a degree of polymerization.

6. A fluorine-containing aryl ether ketone polymer according to claim 4 and represented by the formula (V):

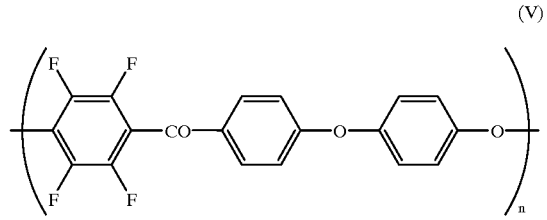
(V)

wherein n stands for a degree of polymerization.

7. A fluorine-containing aryl ether ketone polymer according to claim 4 and represented by the formula (VI):

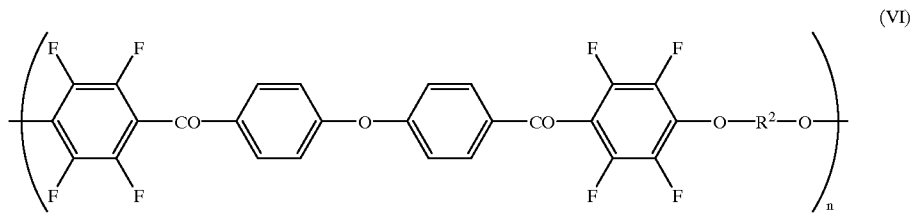
wherein n stands for a degree of polymerization and $R^3$ stands for
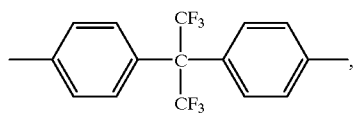
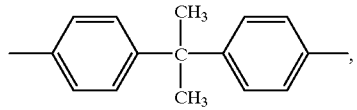
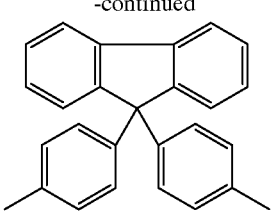
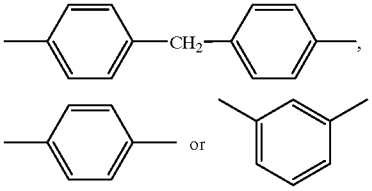
* * * * *